US006666842B1

United States Patent
Sakai

(10) Patent No.: US 6,666,842 B1
(45) Date of Patent: Dec. 23, 2003

(54) DEVICE AND METHOD FOR PERFUSING PERITONEAL DIALYZING FLUID

(76) Inventor: Asahi Sakai, 4-8, Hachimandai 1-Chome, Sakura-Shi, Chiba 285-0867 (JP)

( * ) Notice: Subject to any disclaimer, the term of this patent is extended or adjusted under 35 U.S.C. 154(b) by 0 days.

(21) Appl. No.: 09/806,686
(22) PCT Filed: Oct. 7, 1999
(86) PCT No.: PCT/JP99/05535
§ 371 (c)(1), (2), (4) Date: Apr. 4, 2001
(87) PCT Pub. No.: WO00/20052
PCT Pub. Date: Apr. 13, 2000

(30) Foreign Application Priority Data

Oct. 7, 1998 (JP) .......................... 10-285029

(51) Int. Cl.[7] .......................... A61M 1/00; A61M 37/00; C02F 9/00; B01D 11/00; B01D 61/00
(52) U.S. Cl. ........................ 604/29; 604/5.01; 210/645; 210/651; 210/195.2
(58) Field of Search ........................ 604/29, 4.01, 5.01, 604/5.04, 6.09, 6.11, 6.13, 93.01, 113, 131, 151, 264, 272, 523; 210/644, 645, 646, 649, 650, 651, 767, 175, 181, 194, 195.2, 348, 439, 500.1

(56) References Cited

U.S. PATENT DOCUMENTS 3,707,967 A * 1/1973 Kitrilakis et al. ............. 604/29
4,338,190 A    7/1982 Kraus et al.
4,618,343 A * 10/1986 Polaschegg ................... 604/29
5,141,493 A *  8/1992 Jacobsen et al. .............. 604/29
5,498,338 A *  3/1996 Kruger et al. ............... 210/641
5,660,722 A    8/1997 Nederlof
6,254,567 B1 * 7/2001 Treu et al. ..................... 604/29

* cited by examiner

Primary Examiner—Brian L. Casler
Assistant Examiner—Mark K Han
(74) Attorney, Agent, or Firm—Wenderoth, Lind & Ponack, L.L.P.

(57) ABSTRACT

An instrument for continuous recirculation of peritoneal dialysate to infuse and drain out the dialysate automatically through catheters implanted in a peritoneal cavity of a human body. The instrument includes a prefilter, a primary filter comprising a semipermeable membrane having a maximum permeable molecule of up to 30,000 dalton, a pump for lowering the outside pressure of the primary filter relative to the inside pressure, a secondary filter having a semipermeable membrane having a maximum permeable molecule of 5,000 dalton, a pump for raising the pressure of a supplemental liquor line relative to the inside of a secondary filter line, and a method of recirculating dialysate using the above-mentioned instrument. The recirculation instrument permits the reuse of protein which is permeated out from a patient's body, as an osmotic agent in peritoneal dialysate, in order to maintain a disinfected recirculating line, and to improve an ultrafiltration rate and clearance of uremic toxin.

7 Claims, 4 Drawing Sheets

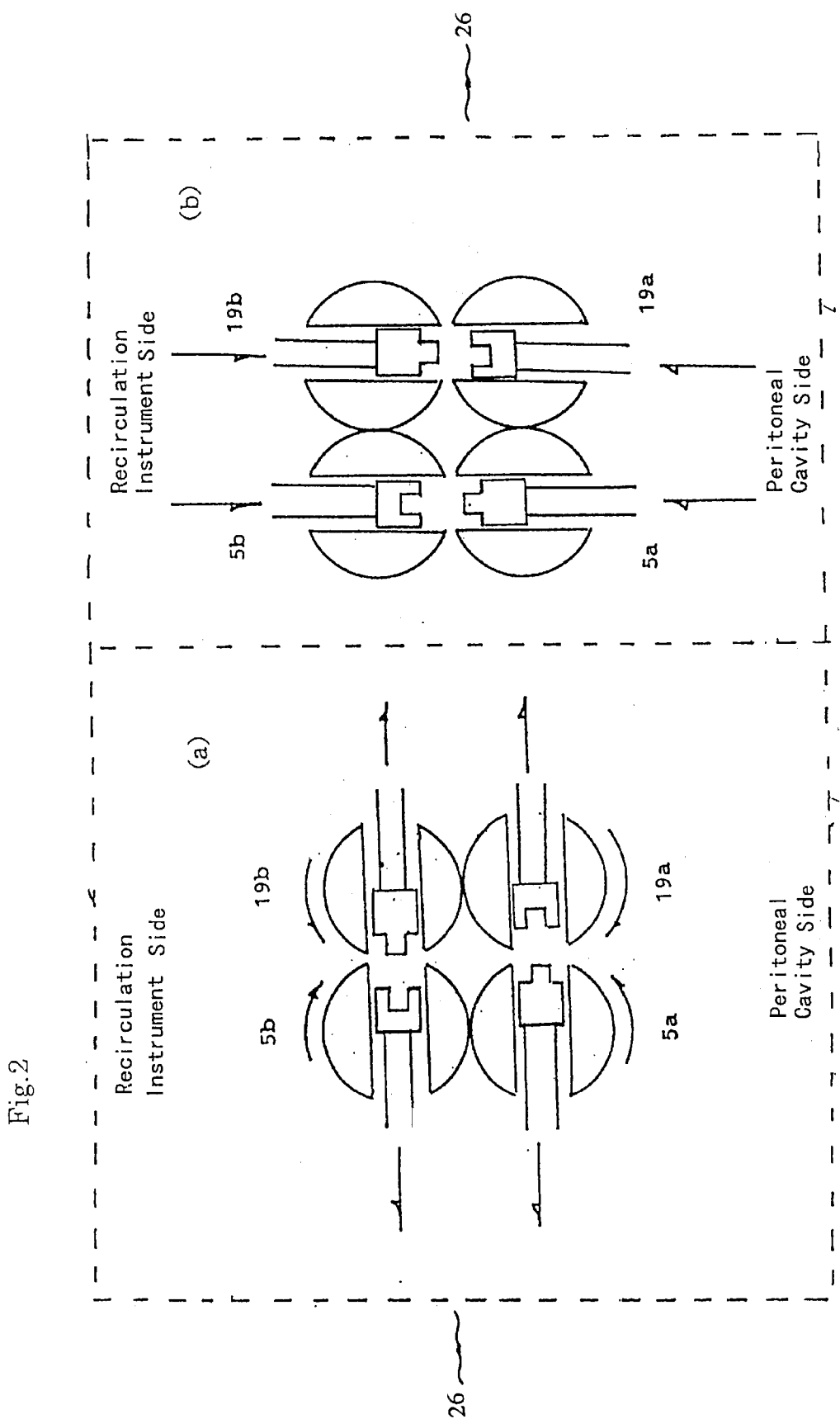

DEVICE AND METHOD FOR PERFUSING PERITONEAL DIALYZING FLUID

BACKGROUND OF THE INVENTION

1. Field of the Invention

The present invention relates to a peritoneal dialysis instrument for improving dialysis efficacy in removing excess liquid and uremic toxin by maintaining polymer osmotic agents in place of glucose in a recirculation line without requiring outside contact for the therapy of chronicle renal failure disease.

2. Description of the Related Art

Peritoneal dialysis has been applied as an effective therapy for renal failure patients. The dialysis is performed so that dialysate is infused into the peritoneal cavity from the dialysate bag through a catheter, which is implanted in the patient's peritoneal cavity, and the dialysate is stored in the cavity for a certain time. Then, the dialysate is drained out through the same catheter. This procedure is repeated a few times a day.

This dialysis has a few advantages over hemodialysis from a physiological point of view, as it purifies blood continuously through the patients' peritoneum, while hemodialysis uses artificial membranes. Also, peritoneal dialysis enables the patients to participate in social activity, and as a result, the dialysis has been widely applied.

In hemodialysis, ultrafiltration is achieved by raising the pressure of the blood line over that of the dialysate line. However, the same method can not be applied to peritoneal dialysis. As a result, an osmotic agent is added into the dialysate so as to raise the osmotic pressure of the dialysate over that of plasma, and the dialysate is infused into the peritoneal cavity so as to contact it to the peritoneum for removing excess liquid from the patient's body. For this purpose, glucose has been used as an osmotic agent. However, adverse effects such as the disfunctioning of the, peritoneum due to the absorption of such a large quantity of the osmotic agent into the patient body are now recognized as a serious problem.

For solving the aforementioned problem, the inventor of the present invention has proposed an instrument and a method by which serum protein, such as albumin, globulin and the like which are permeated out through peritoneum into the dialysate, is recovered and refined, and is then concentrated and reused with dialysate as the most physiological substitutes of glucose.

In these proposed processes, the following were disclosed:

(A) A method to dissolve the recovered and refined protein in dialysate after which low molecular weight uremic toxin substances not higher than 30,000 daltons are removed by the repeated concentration/dilution procedures with a semipermeable membrane, and to reuse it as a substitute of glucose. (Japanese Laid Open Patent Application Hei 9-327511)

(B) A method to keep the abovementioned device and the components disinfected. (Japanese Laid Open Patent Application Hei 10-85324)

(C) A method to separate the malignant solute in the solvent and refine the protein by acidifying the protein and then de-acidifying it through water dialysis so as to deposit it at iso-electric pH (Japanese Laid Open Patent Application Hei 9-302388)

Also, for carrying out the invention (C), it was disclosed that the device comprises the followings:

(D) An inflow line having a filter whose maximum pore size is 100–300 nanometers for preventing bacteria invasion into the peritoneal cavity; and (E) A two step prefilter having a pore size between 5 and 200 microns to remove blood cells, peritoneum mesothelial cells, fibrin and the like suspended in the effluent when it is drained out from peritoneal cavity.

A few attempts have been reported to utilize serum protein in ascites (Hwang, E. R., Richard, D. O. Sherman, A. et al., Dialytic Ascites Ultra-filtration in Refractory Ascites, Am. J. Gastroenteral, 77(9): 652–654, 1982, for example)

However, they did not refer to removing uremic toxin, because their target was not a renal failure patient.

Also, a method to add a peritoneum protecting component of a molecular weight of not higher than 3,000 daltons recovered from peritoneal dialysis effluent into dialysate (Japanese Laid Open Patent Application Hei 8-337590). However the recovery and reuse of the component of the molecular weight higher than 3,000 daltons is not suggested.

When plasma protein that is permeated out of the patient body is reused as an osmotic agent in place of glucose, the following conditions need to be satisfied:

(I) To minimize the contact with atmosphere and foreign matters so as to not denature the protein;

(II) To minimize plugging the semi-permeable membrane on the recirculation line, and to decrease the frequency of exchange; and (III) To completely prevent the invasion of pathogenic bacteria and endotoxin.

For the solution of the aforementioned (I) problem, it may be suggested that a filter is set at the exit of the catheter, or, as a further perfect protection, a hollow fiber type semi-permeable membrane is set in a peritoneal cavity in order to keep the polymer in the peritoneal cavity. However, in those cases, complicated preventive means are required to avoid plugging of the membrane, and the exchange of the filter requires skillful care.

SUMMARY OF THE INVENTION

The present invention has developed a practical method and an instrument for solving the aforementioned problems, by the combination of either one of the following technologies:

[I] The drained dialysate is warmed up to a preset temperature, and then it is filtered through a prefilter for removing foreign materials so as to prevent the plugging of the filter.

[II] A semi-permeable membrane (having a cut-off point of up to 30,000 dalton) filter is used for removing uremic toxin of low molecular weight and of middle molecular weight.

[III] A supplemental electrolyte solution is supplied through a semi-permeable membrane filter (having a cut-off point of up to 5,000 dalton) for preventing the infection and invasion of endotoxin.

Also, the present inventor has found that by the use of the device, dialysate may be drained out of the peritoneal cavity and may be recirculated in a closed line. In addition, a portion of the dialysate may be filtered out through a semi-permeable membrane to remove malignant component, and then, a fresh dialysate may be supplemented through a semipermeable membrane and returned automatically into the peritoneal cavity.

Briefly, the present invention relates to an instrument-that comprises (a) a prefilter, (b) a first filter that comprises a semi-permeable membrane having a maximum permeable molecule of up to 30,000 dalton, (c) a pump to lower the outside pressure of the first filter (b) relative to the inside pressure, (d) a second filter that comprises a semi-permeable membrane having a maximum permeable molecule of 5,000 dalton, (e) and a pump to raise the pressure of a supplemental liquor line relative to the inside line of the second filter.

Also, the present invention relates to a method characterized in that dialysate is drained out of the peritoneal cavity and recirculated in a closed line, and a portion of the dialysate is filtered out through a semi-permeable membrane. Then, an equivalent volume of fresh dialysate is supplemented through a semi-permeable membrane having a maximum permeable molecule of 5,000 dalton and is then returned into the peritoneal cavity.

As a favorable embodiment for carrying out the present invention, the following technologies may be adapted:

(1) A bacteria-free filter (having a maximum pore size of 100–300 nanometers) is set up on the peritoneal cavity side of the inflow line's joint.

(2) Dialysate in the peritoneal cavity is recirculated through a perfectly closed and continuously connected and previously disinfected line for keeping the protein not denatured in the automatic dialysate recirculation instrument.

(3) A reverse flow prevention valve (anti-reverse flow valve) is set up on the withdrawn line.

(4) A closed chamber, of which the inside can not directly be contacted by fingers, is set up for disconnection and connection procedure by remote operation from outside, after the infusion of dialysate for the daytime cycle before getting up in the morning.

BRIEF DESCRIPTION OF THE DRAWINGS

FIG. 2 illustrates an exchanging method of an outflow line joint and an inflow line joint for:

Figure 1:
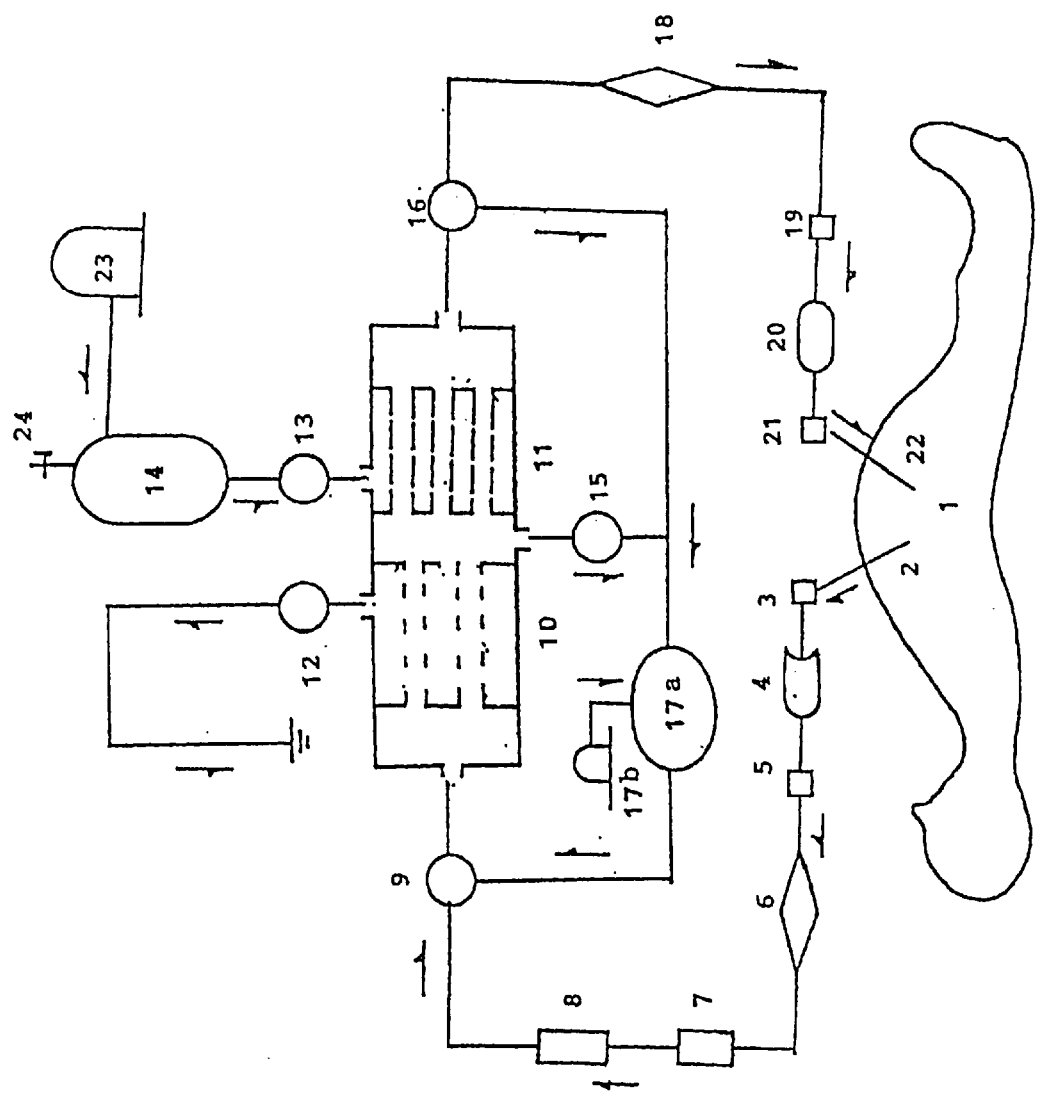
FIG. 1 illustrates a Peritoneal Dialysate Recirculation Circuit in a nighttime state where the peritoneal dialysate recirculation instrument is connected with the patient's outflow and inflow catheters, respectively, and the dialysate is recirculated.
Figure 1A:
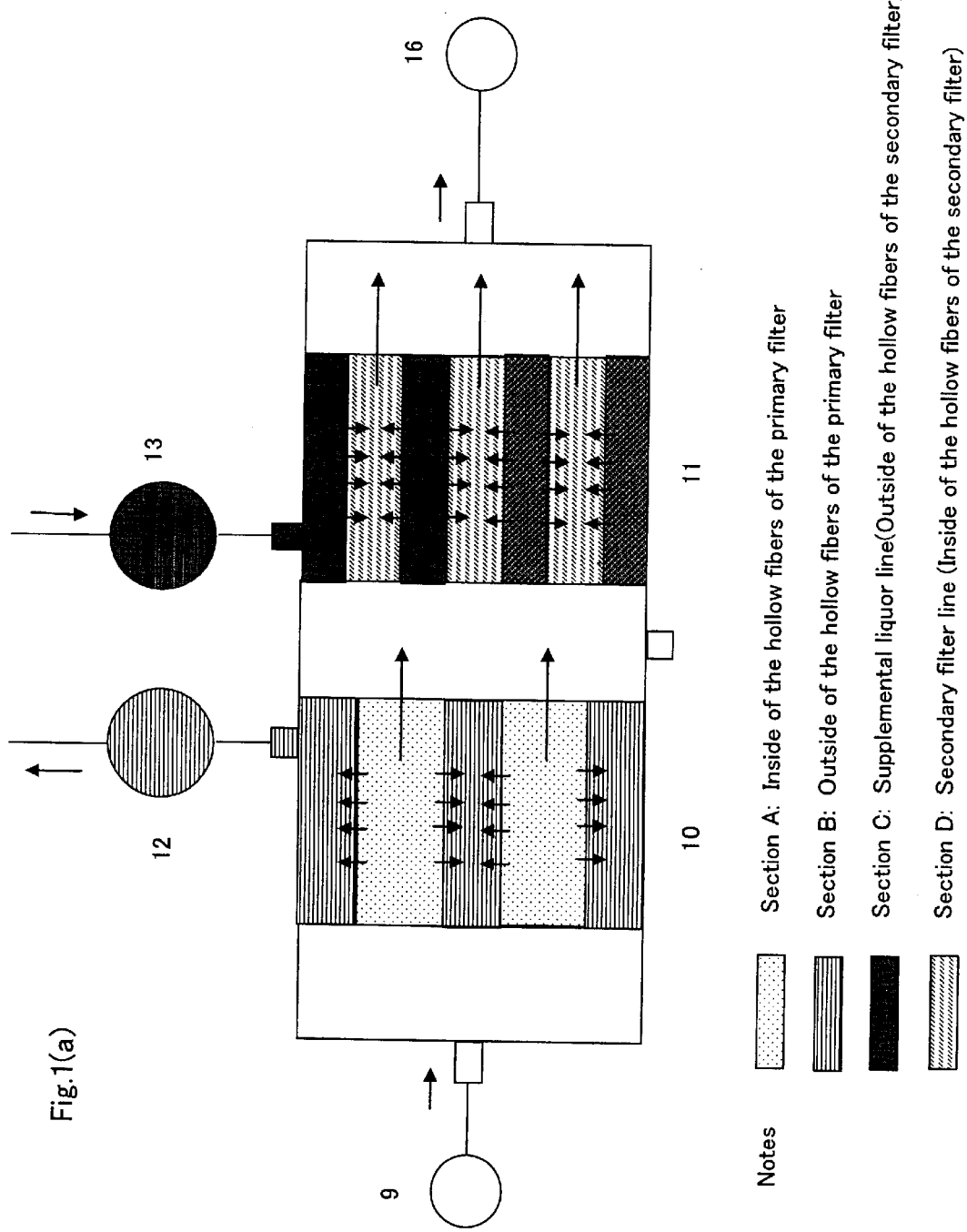
FIG. 1(a) is an enlargement of the structure of the primary filter and the secondary filter of FIG. 1 and illustrates the flow of the dialysate and a supplemental solution therethrough.

(a) a disconnecting operation of the joint, which has been directly connected in the daytime (FIG. 3), and a rotation operation of the parts; and (b) a rotating operation of the disconnected part so as to face the part of peritoneal cavity side and the part of recirculation instrument side, and a connecting operation of the parts so as to make ready for nighttime recirculation (FIG. 1).

Figure 3:
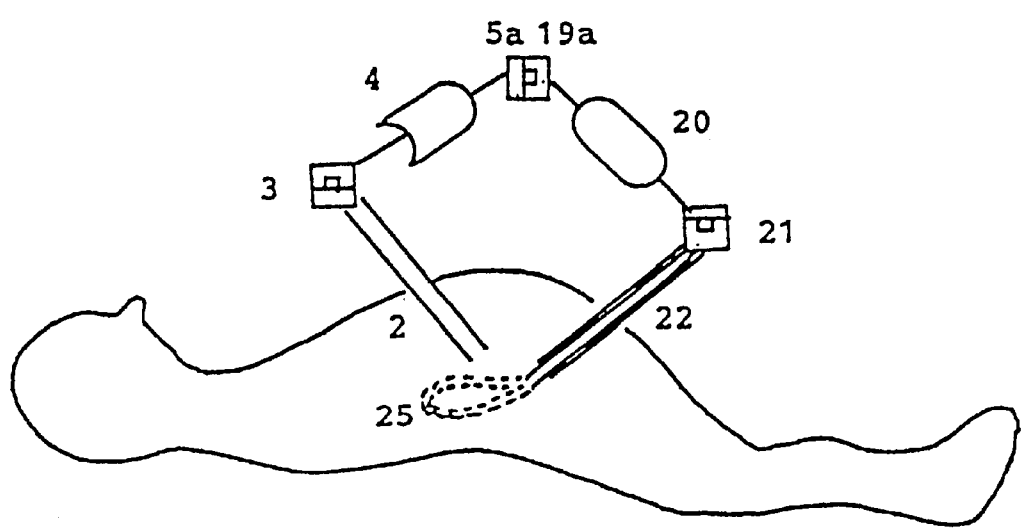

FIG. 3 illustrates an O-shaped circuit of the catheter at an extracorporeal side (during a daytime state when the patient leaves and is away from the recirculation instrument for daily life) and hollow fibers in the peritoneal cavity.

EXPLANATION OF THE REFERENCE NUMERALS

1. Peritoneal Cavity
2. Outflow Catheter
3. Joint
4. Anti-Reverse Flow Valve
5. Outflow Line Joint
   5a. Patient Peritoneal Cavity Side Terminal of Outflow Line Joint
   5b. Recirculation Instrument Side Terminal of Outflow Line Joint
6. Heater
7. Prefilter
8. Bacteria-free Filter
9. Pump
10. Primary Filter
11. Secondary Filter
12. Suction Pump
13. Feeding Pump
14. Supplemental Solution Vessel
15. Pump
16. Pump
17a. Container
17b. Reservoir of Osmotic Agents
18. Warmer
19. Inflow Line Joint
   19a. Patient Peritoneal Cavity Side Terminal of Inflow Line Joint
   19b. Recirculation Instrument Side Terminal of Inflow Line Joint
20. Bacteria-free Filter
21. Joint
22. Inflow Catheter
23. Reverse Osmosis Membrane Water
24. Inlet Valve of Chemicals
25. Loupe-shape Hollow Fibers
26. Isolated Case

DETAILED DESCRIPTION OF THE INVENTION

The present invention will be explained with reference to FIG. 1.

FIG. 1 illustrates an outflow catheter 2 and an inflow catheter 22 in a peritoneal cavity 1.

It happens to be observed often that when liquor is recirculated from an inflow entrance to an outflow exit at a consistent rate, a localized flow, a so-called channeling, is formed in the peritoneal cavity; then, a portion of the liquor tends to stay at "dead spaces". For solving this problem, a certain number of loop-shaped porous hollow fibers 25 are fixed at the end of the inflow catheter so that the dialysate may flow throughout the cavity as illustrated in FIG. 3. Instead of an outflow catheter 2, an outer lumen of a concentric double lumen catheter may alternatively be used.

Outflow catheter 2 comprises joint 3, anti-reverse flow valve 4, and outflow joint 5, and the flow catheter is connected with heater 6 and prefilter 7 in series.

Outflow joint 5 comprises peritoneal side part 5a and instrument side part 5b, as illustrated in FIG. 3. During recirculation time, which occurs at night, the parts 5a and 5b are connected together. The joint 5 has the structure of male/female parts, which are directly adaptable to each counterpart of inflow joint 19, as is discussed further below. During the daytime, which is when dialysate is not recirculated but is stored in the peritoneal cavity, the joint part 5a is connected with the joint part 19a, and the joint part 5b is connected with the joint part 19b, thereby forming the circuit illustrated in FIG. 3.

The dialysis effluent that is drained out of the patient's peritoneal cavity contains peritoneum mesothelium cells, leucocyte cells, deposited fibrin, and the like. These foreign particles may be separated from the filtrate with prefilter 7.

Fibrinogen in the dialysate effluent tends to be deposited out as fibrin after prefiltration, and it plugs the filter. This has often been experienced when plasma and humor is filtered. For preventing the plugging problems, it is desirable to warm up the effluent up to 55–60° C. by means of a heater before prefiltration.

After the dialysate is passed through a bacteria-free filter 8, it is flown by pump 9 to the first filter 10 and then to the second filter 11. The first filter has a semi-permeable membrane of a maximum permeable molecule of up to 30,000 dalton, greater than that of 2-microglobulin, for example. By filtering out a portion of the dialysate through this filter, middle molecule malignant components, such as a 2-microglobulin of the molecular weight of 11,800 daltons, may be removed.

After filtering through the first filter, the partially filtered dialysate is supplemented with a supplemental electrolyte solution. The supplemental solution is added through the second filter whose semipermeable membrane does not pass endotoxin. The second filter has a semipermeable membrane of a maximum permeable molecule of up to 5,000 dalton so that it can prevent invasion of bacteria and endotoxin.

Endotoxins are lipopolysaccharides, of which the largest ones have a molecular weight of a few hundred thousand dalton. The smallest lipopolyssaccharides have a molecular weight of 6,000–8,000 dalton. On the other hand, supplemental chemicals and additives are lighter molecules, such as 1,000 dalton, so that they may pass through this semipermeable membrane of the second filter 11.

Due to the reduced pressure in the outside of the first filter 10 by suction pump 12, dialysate in the first filter 10 is suctioned out. The supplement solution in the second filter is pressed by feeding pump 13 to feed in through the second filter 11. The filtration in both filters is accelerated by these pumps 12 and 13.

FIG. 1(*a*) illustrates an enlargement of the structure of the primary filter 10 and the secondary filter 11, and the flow of the dialysate and the supplemental solution. As shown in FIG. 1(*a*), the primary filter 10 and the secondary filter 11 each comprise a number of hollow fibers. The sections labeled as Section A are inside the hollow fibers which lead the dialysate rightward to the secondary filter 11. The sections labeled as Section B are outside of the primary filter 10 and lead the suctioned filtrate upward to be discarded by the suction pump 12. The individual sections of Section B appear to be isolated, but in fact, they are in a continuous space leading to the suction pump 12. In the suctioned filtrate, middle molecules of less than 30,000 dalton are thereby removed as indicated by the upward arrow from primary filter 10 to the suction pump 12.

The supplemental solution is stored in a supplemental solution vessel 14, and it is sent to the second filter by feeding pump 13 as indicated by the downward arrow from the supplemental solution vessel 14 and the supplemental liquor line (sections labeled as section C of the secondary filter 11) into the secondary filter line (sections D on the inside of the hollow fibers of the secondary filter 11). Amino acids, fatty acids, glucose, peptides or any mixture thereof are added into the supplemental solution through a line which is connected with a valve 24 that is equipped in the supplemental solution vessel 14.

The above-mentioned supplemental solution may be:
(a) a commercially available infusion solution or peritoneal dialysate which is sterilized and packed in a supplemental solution vessel 14, or
(b) a hemodialysis concentrate or dry chemicals for hemodialysis, which is diluted or dissolved with, reverse osmosis water.

After partial filtration in the first filter 10 and supplementation at the second filter 11 the dialysate is flown by pump 16 through a warmer 18, where it is warmed up to a standard corporeal temperature. Then, the dialysate is infuised through inflow joint 19, bacteria-free filter 20, and joint 21 so as to pass into peritoneal cavity 1.

On the by-pass line 15-17*a*-9, a container 17*a* is set up, where a portion of polymer components, which is stored in the peritoneal cavity during the daytime, may be stored. The solution can be circulated through the line by pump 15 so as to repeat the concentration/dilution procedures. A cooling or freezing unit may be equipped for the container 17*a*.

One of the present invention's aims is the reuse of recovered plasma protein permeated from a patient's body through peritoneum into the dialysate.

However, in the case where the recovered protein is not enough to achieve sufficient ultrafiltration, other osmotic agents may be supplemented. Such supplemental agents may be high or low molecular weight substances.

High molecular weight substances maybe oligosaccharides, and low molecular weight substances may be glucose or amino acids. Even when substances whose daily dose is restricted are used, usage is within a tolerable quantity, and those osmotic agents may be used so that the required osmotic pressure can be obtained. Low molecular weight agents are added from a supplemental reservoir 14, and high molecular weight agents are supplied from an osmotic agent reservoir 17*b* into the container 17*a*, where the additives are mixed with the dialysate.

The recirculation instrument is connected with peritoneal catheters at night so as to automatically achieve peritoneal dialysate recirculation. However, in the daytime, joint 5 and joint 19 are disconnected from the recirculation instrument and form a daytime circuit as illustrated in FIG. 3. For such a disconnection and connection operation, each joint comprises a respective part a and part b as illustrated in FIG. 2. That is, joint 5 consists of parts 5*a* (male) and 5*b* (female), and joint 19 consists of parts 19*a* (female) and 19*b* (male). When parts 5*a* and 5*b* are disconnected from each other and parts 19*a* and 19*b* are disconnected from each other, parts 5*a* and 19*a* can be connected and parts 5*b* and 19*b* can be connected as illustrated in FIG. 3. According to the present invention, outflow joint 5 and inflow joint 19 are set up adjacently in an isolated case 26 and manipulated from outside of the case to be isolated and free from human contact.

By use of the recirculation instrument according to the present invention, extraperitoneal recirculation procedures may be achieved continuously and automatically in the following way. First, before the patient begins sleeping, parts 5*a* and 19*a* and parts 5*b* and 19*b*, which have been respectively connected in the isolated case 26 during the daytime, are disconnected. Then, each part is rotated by 90 degrees to the direction along the arrows as illustrated in FIG. 2. Then, parts 5*a* and 5*b* are connected, and parts 19*a* and 19*b* are connected to form a recirculating circuit as illustrated in FIG. 1.

When the circuit line is set up, recirculation is started. After concentrating the drained dialysate and removing uremic toxin in the first filter, a portion of the concentrate is stored in the container 17*a*.

The remaining concentrate is added to a fresh electrolyte solution through the second filter 11, and then is infused into the peritoneal cavity. If needed, concentrating/diluting procedures are repeated a few times through a circulation circuit (16-17*a*-9). In some cases, an electrolyte solution, such as amino acids, glucose, fatty acids, or peptides, etc., is added.

Not only sodium caprilate and N-acetyltryptophan are added as stabilizers to prevent the recycled protein from becoming denatured, but acids, alkali, and anti-oxidants, such as, glutathione, vitamin C, vitamin E and reductants, are also added to the electrolyte solution so as to release urea, bilirubin, and S—S bonded chemicals that are attached to cysteine, $34^{th}$ amino acid from N-terminal of albumin. By making albumin as active as those of healthy persons by the abovementioned way before infusing it into the peritoneal cavity, it may thereby improve the therapy effect.

Thus, the dialysate in the peritoneal cavity is consistently drained out, and is substituted partly with a fresh electrolyte solution by the way of recirculation at night when the patient sleeps.

Before getting up in the morning, all or almost all of the dialysate in the peritoneal cavity is drained out, and the drain is repeatedly concentrated and diluted. Then, the aforementioned chemicals are added and infused into the peritoneal cavity. The joints 5 and 19 are disconnected to form a circuit as illustrated in FIG. 3 by directly connecting the corresponding part of joint 5 with the corresponding part of joint 19. Briefly, as in FIG. 3, on the catheter side, an "O" shaped circuit is formed. On the catheter side, part 19a is connected to a bacteria-free filter entrance 20 on the inflow line, and part 5a is connected to an anti- reverse flow-valve exit 4 on the outflow line. On the recirculation instrument side, the counter parts 5b and 19b are connected.

The above-mentioned operation can be manipulated in a separate case so as to prevent human contact, and through which a continuous recirculation of the dialysate can be performed.

By use of the instrument according to the present invention, continuous recirculation can be achieved simultaneous to a partial substitution of the dialysate.

By the instrument according to the present invention, safely reusing the permeated out protein into the peritoneal dialysate, and continuous recirculation of the dialysate can be achieved in the simplest way. Briefly, every day, dialysate is drained out and infused through a semipermeable membrane, and solution flows through a completely closed circuit line so as to minimize the risk of infection.

By the instrument according to the present invention, continuous recirculation of the dialysate can be achieved simultaneous to a partial substitution. As a result, continuous draining of the dialysate out of the peritoneal cavity and partial substitution of the dialysate with fresh electrolyte solution can be achieved during the nighttime when the patient sleeps. After getting up in the morning, the patient can be disconnected from the instrument and thereafter enjoy a daily life in the daytime without being connected to an external instrument.

It has been said that increasing the number of dialysis cycles per day is effective for improving the dialysance of peritoneal dialysis. However, too many cycles of peritoneal dialysis increases the vacancy time of a peritoneal cavity. To solve this problem, the use of tidal type recirculation has been proposed. However, tidal type recirculation leaves a portion of liquid in the peritoneal cavity, and it can not improve the dialysance significantly.

The present invention, in contrast, can improve the dialysance, as the dialysate recirculates without a vacancy time in the peritoneal cavity. Another recirculating method in which the dialysate is refined by extraperitoneal dialysis by use of an artificial dialyser and extracoporial dialysate can improve the dialysance, but this recirculating method requires a large volume of dialysate. The present invention provides a much more economical dialysis due to a partial substitution of recirculated dialysate. This advantage is also valid in the case where no polymer component is contained and recycled.

Instead of requiring large volumes of dialysate to be delivered, on site preparation of dialysate by diluting the dialysate concentrate or by dissolving dry chemicals is very effective for reducing the cost of therapy. The water preparation device for the dissolution and dilution by reverse osmosis membrane may be equipped in the instrument according to the present invention so as to provide a safe and low cost dialysate.

Infection can be prevented by the use of a previously connected, packed and sterilized extracorporeal recirculation line. Also, the infection rate at a periodical exchange can be significantly reduced by having the outflow and inflow connection parts fixed adjacent to one another in a closed case as illustrated in FIG. 2, and the connection parts can be disconnected and exchanged by outside manipulation free from contact of the atmosphere and other foreign, e.g. human, contact.

By using the above-described method and instrument, the present invention enables (I) minimizing contact with the atmosphere and other foreign matters such as human contact, (II) minimizing the plugging of the semi-permeable membrane on the recirculation line, and (III) perfectly preventing the invasion of bacterial and endotoxin from external sources.

What is claimed is:

1. An instrument for continuous recirculation of peritoneal dialysate to infuse and drain out the dialysate automatically through catheters implanted in a peritoneal cavity of a human body, said instrument comprising:

a prefilter;

a primary filter located downstream of said prefilter, said primary filter being operable to filter out a portion of the dialysate, and said primary filter comprising a semipermeable membrane having a maximum permeable molecule of up to 30,000 dalton;

a suction pump operable to lower an outside pressure of said primary filter relative to an inside pressure of said primary filter;

a feeding pump operable to supply a fresh dialysate; and a secondary filter located downstream of said feeding pump, said secondary filter being operable to filter out a portion of the fresh dialysate, and said secondary filter comprising a semipermeable membrane having a maximum permeable molecule of up to 5,000 dalton.

2. The instrument for continuous recirculation of peritoneal dialysate according to claim 1, wherein a supplemental liquor line provides communication between said feeding pump and said secondary filter.

3. The instrument for continuous recirculation of peritoneal dialysate according to claim 2, wherein said feeding pump supplies the fresh dialysate to said secondary filter through the supplemental liquor line, said feeding pump being further operable to raise the pressure of the supplemental liquor line relative to an inside pressure of said secondary filter.

4. The instrument for continuous recirculation of peritoneal dialysate according to claim 1, wherein the instrument is equipped with a dialysate recirculation line that is replaceable, made of flexible material, prefabricated as a continuous line from an outflow terminal to an inflow terminal, and sterilized.

5. The instrument for continuous recirculation of peritoneal dialysate according to claim 4, further comprising an outflow joint and an inflow joint which can be directly connectable to each other, and in an isolated case the outflow and inflow joints can be fixed adjacent to each other so that terminals of a recirculation instrument side and terminals of a patient peritoneal cavity side may be disconnected and connected by remote handling free from human contact.

6. The instrument for continuous recirculation of peritoneal dialysate according to claim 1, further comprising an outflow joint and an inflow joint which can be directly connectable to each other, and in an isolated case the outflow and inflow joints can be fixed adjacent to each other so that terminals of a recirculation instrument side and terminals of a patient peritoneal cavity side may be disconnected and connected by remote handling free from human contact.

7. The instrument for continuous recirculation of peritoneal dialysate according to claim 1, wherein said prefilter, which is located upstream of said primary filter, is operable to prevent said primary filter from becoming plugged by cells and fibrin in the dialysate withdrawn from the peritoneal cavity.

\* \* \* \* \*